US00PP08468P

United States Patent [19]

McGredy

[11] Patent Number: Plant 8,468

[45] Date of Patent: Nov. 23, 1993

[54] MINIATURE ROSE PLANT NAMED 'MACMOSCO'

[76] Inventor: Samuel D. McGredy, 130 B Beach Rd., Castor Bay, Auckland 9, New Zealand

[21] Appl. No.: 637,000

[22] Filed: Jan. 3, 1991

[51] Int. Cl.[5] ..... A01H 5/00

[52] U.S. Cl. ..... Plt./7

[58] Field of Search ..... Plt. 7

[56] References Cited

U.S. PATENT DOCUMENTS

P.P. 4,029 3/1977 Moore ..... Plt. 7

P.P. 4,867 7/1982 Moore ..... Plt. 7

P.P. 5,328 11/1984 Moore ..... Plt. 7

*Primary Examiner*—James R. Feyrer

[57] ABSTRACT

A new and almost continuously and profusely blooming rose plant, of the miniature class, having conspicuous, open-faced flowers with petals of gently rounded shape but having a minute point on the centerline interrupting the otherwise rounded profile of the margin; such petals of pleasing, contrasting white and red stripes; the flowers being pleasantly highlighted by their placement over a healthy and dense crop of glossy, deep green foliage on an upright compact but vigorously growing, well branched plant.

1 Drawing Sheet

BACKGROUND OF THE INVENTION

The present invention relates to a new and distinct variety of rose plant of the miniature rose class which was originated by me by crossing, as the seed parent, the miniature plant 'Mighty Mouse' with, as the pollen parent, the rose plant known as 'Hurdy Gurdy'. Upon recognition of the attributes of this plant within the progeny of such cross, it was selected for further testing and observation. Upon recognition that this plant was novel and expressed numerous superior and desirable traits to be specified below, the plant of this application was assigned an international recognition name of 'Macmosco'. This plant has been asexually reproduced by me or by my direction by both rooting cuttings and by budding an Washington County, Oreg. Clones so produced have been substantially and reliably identical to the original selection in every distinguishing characteristic, establishing that the plant is stable.

Specimens described below were grown in Washington County, Oreg.

SUMMARY OF THE INVENTION

The new plant of this invention contains a number of outstanding attributes in combination which set it apart from all other plants of the miniature rose market class. Such characteristics may be summarized as follows:

A new and conspicuously attractive flower having striped red on white petals.

Petals of gently rounded shape and of pleasing characteristicly contrasting and random patterns of red stripes on a white background, and having a small point at the center of the rounded apex of the margin.

Open faced flowers which open to a substantially flat form.

Flowers being pleasantly highlighted above lush, dense foliage which is healthy in appearance.

A plant which is highly remontant and blooms almost continuously and profusely.

Flowers formed singly or in sprays placed over a healthy and dense crop of glossy, deep green foliage on an upright compact but vigorously growing, well branched plant.

BRIEF DESCRIPTION OF THE DRAWING

The single sheet of photographic drawing depicts the buds and open-faced flowers of 'Macmosco' in various stages of maturity; the flower stems of the plant and the vegetative growth and foliage characteristics of the plant in colors as true as is reasonably possible in color illustrations of this nature.

Color definations used in the descriptions to follow have been taken from The *R.H.S. Colour Chart* by The Royal Horticultural Society, London.

BOTANICAL DESCRIPTION OF THE PLANT

The following botanical descriptions are based on specimens of the plant as observed growing out doors in Washington County, Oreg., during the month of July.

Parentage:

*Seed parent.*—'Mighty Mouse'.

*Pollen parent.*—'Hurdy Gurdy'.

Classification: Miniature.

FLOWER

Blooming habit: Nearly continuous, with blooms occuring both singly and in clusters of up to about 5 to 7.

A. Buds:

(1) *Size.*—About 1¼ cm long.

(2) *Form.*—Pointed; no foliaceous appendages.

(3) *Color.*—The reverse of the petal portions showing is white (near R.H.S. 155A) with slight stripes of red (near R.H.S. 47A).

(4) *Sepals.*—Permanent, spear shaped and reflexing with flower opening; color of outside surfaces being green (R.H.S. 135C); inside surfaces covered with a dense tomentum and have a white to silver cast.

(5) Peduncle.—Length: About 3½ cm. Aspect: Straight. Strength: Erect. Color: Green (near R.H.S. 137C)

B. Bloom:

(1) *Size.*—About 3½ cm. when fully expanded.

(2) *Borne.*—Singly and as sprays in clusters of 5 to 7 flowers.

(3) *Form.*13 Slightly cupped initially, progressively becoming flat with advanced opening; slight reflexing of the petals.

(4) *Petalage.*—18 under normal conditions.

(5) *Color.*—Novel. Stripes of white and red (near about R.H.S. 47A to 51A over R.H.S. 155D).

C. Petals:

(1) *Texture.*—Moderately thick and of good substance.

(2) *Appearance.*—Velvety both inside and outside.

(3) *Form.*—Blooms have a flat form with shallow depth; petals stand at right angles to the axis of the calyx of individual flowers. Individual petals are symmetrical and contain a minute point at the central portion of the apex which interrupts the generally rounded profile of the outer margin.

(4) *Arrangement.*—Regularly arranged to form substantially semi-double flowers. (5) *Petaloids in center.*—Few, of irregular shape, generally much smaller than and of the same coloration as petals.

(6) Persistence.—Petals drop off cleanly.

(7) *Fragrance.* Very slight.

(8) *Lasting quality.*—Blooms last 5 days as cut flowers or when left on the bush.

REPRODUCTIVE ORGANS

A. Stamens, filaments and anthers:

(1) *Arrangement.*—Regularly arranged stamens around and superior of pistils. Flower center is plainly visable in open flower.

(2) *Color.*—Medium yellow, aging to a darker yellow.

B. Pollen: Color is medium yellow.

C. Styles: Even length, interose.

D. Stigmas: Of medium yellow coloration.

E. Hips: Develop to about 1 cm in width.

F. Sepal shape: Permanent, spear shaped, reflex with opening of the blossom. Color is green (near R.H.S. 137C).

PLANT

A. Form: bushy, dense, rounded.

B. Growth:

(1) *Branching.*—Upright stems. Uniform; pinching induces further branching.

(2) *Vigor.*—Medium.

(3) *Height.*—Plants attain about 40 cm.

C. Foliage:

(1) *Character.*—Compound, normally 5 leaflets.

(2) *Leaflet size.*—1¾ cm.

(3) *Quantity.*—Abundant.

(4) *Color.*—New foliage is green (near R.H.S. 135C) maturing to a deeper green (near R.H.S. 137B).

(5) *Shape.*—Oval pointed, supported by short petiolule.

(6) *Margin.*—Serrated.

(6) *Serrations*—Serrulate.

(9) *Leaf Stem Color.*—Green (near R.H.S. 135C).

(10) *Stipules.*—Slightly bearded and about ½ cm long.

(11) *Rachis.*—Upper side grooved and about 1 cm long; medium green coloration.

(12) *Resistance to disease.*—Blackspot: Average. Mildew: Average. Rust: Average.

D. Wood:

(1) *New wood.*—Light green color (about R.H.S. 137B) with smooth bark.

(2) *Old wood.*—Green color (about 136B) with smooth bark, about 3 cm internode spacing and sturdy.

E. Thorns:

(1) *Quanity.*—Average on main stalk and laterals.

(2) *Form.*—Dilated at base and declining.

(3) *Length.*—⅓cm.

(4) *Color.*—Rose, turning brown at maturity.

(5) *Position.*—Ordinary.

F. Prickles: Average.

G. Winter hardiness: Requires ordinary protection in extreme cold weather.

I claim:

1. A new and distinct variety of miniature rose plant substantially as described and illustrated, which is particularly characterized by being easy to propagate, vigorous, hardy, bushy or upright habit; having blooms borne singly or in sprays from 5 to 7 which open quickly to a flat form showing yellow stamens; as having petals of conspicuosuly contrasting white and red stripes; and, the flowers being pleasingly highlighted by their placement over a dense crop of lush, deep green foliage.

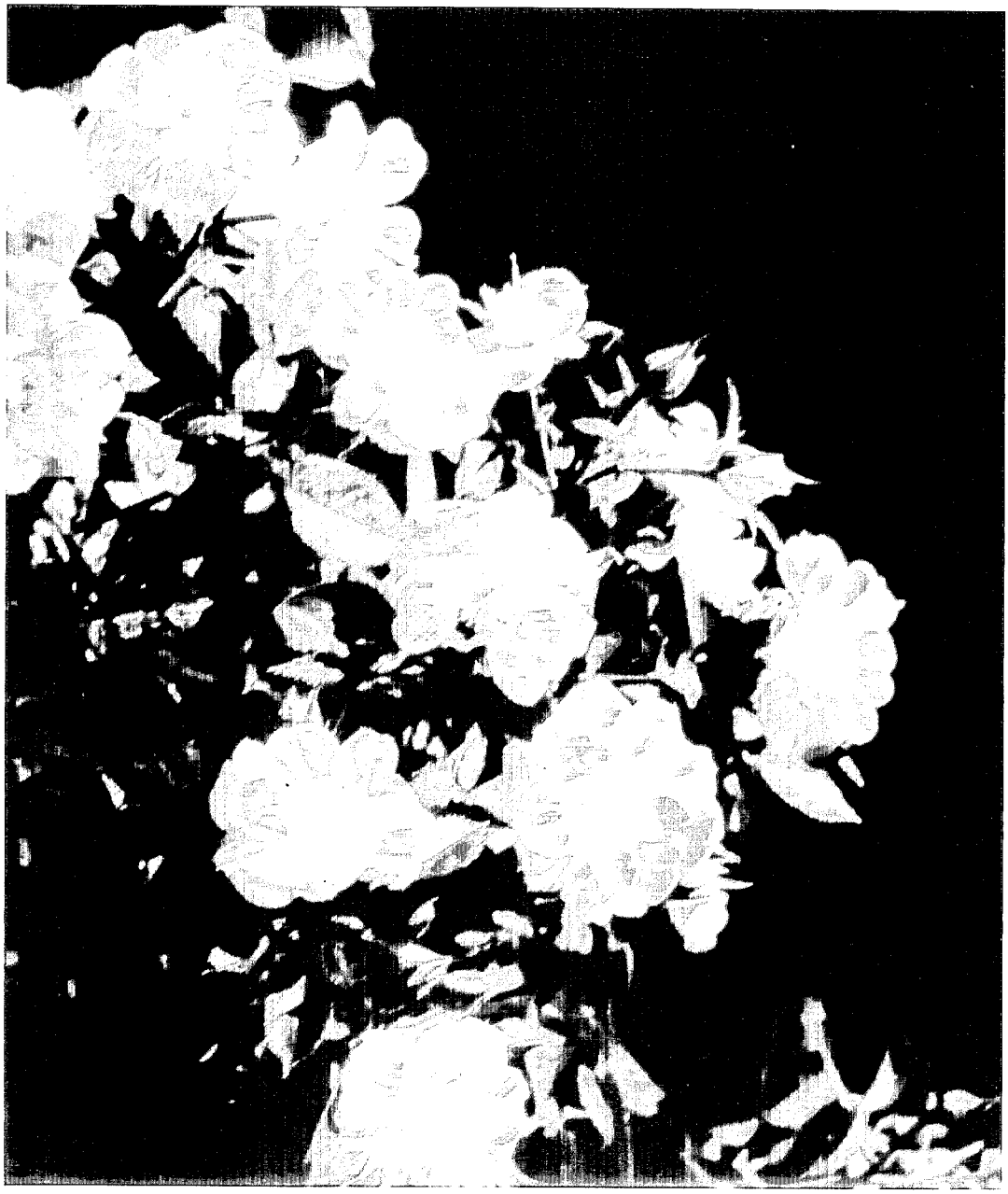

* * * * *